United States Patent [19]
Goldman et al.

[11] Patent Number: 5,932,198
[45] Date of Patent: Aug. 3, 1999

[54] α-AMIDES OF L-AMINO ACIDS AS FRAGRANCE PRECURSORS

[75] Inventors: Virginia Streusand Goldman, Potomac; Judith Wolfe Laney, Silver Spring; Charles W. Slife, New Market, all of Md.

[73] Assignee: The Gillette Company, Boston, Mass.

[21] Appl. No.: 08/990,988

[22] Filed: Dec. 15, 1997

[51] Int. Cl.⁶ .............................. A61K 7/32; A61K 7/06; A61K 7/15; A61K 7/00
[52] U.S. Cl. ........................ 424/65; 424/70.1; 424/73; 424/401; 512/1; 512/25; 562/553
[58] Field of Search .......................... 424/65, 70.1, 73, 424/401; 512/1, 25; 562/553

[56] References Cited

U.S. PATENT DOCUMENTS

| | | |
|---|---|---|
| 4,089,942 | 5/1978 | Bore et al. . |
| 4,934,609 | 6/1990 | Lindauer et al. . |
| 5,176,903 | 1/1993 | Goldberg et al. . |
| 5,223,251 | 6/1993 | Nicholas . |
| 5,380,707 | 1/1995 | Barr et al. . |
| 5,431,904 | 7/1995 | Laney . |
| 5,514,671 | 5/1996 | Lyon et al. ............... 514/104 |
| 5,538,719 | 7/1996 | Preti et al. . |
| 5,626,852 | 5/1997 | Suffis et al. . |

FOREIGN PATENT DOCUMENTS

| | | |
|---|---|---|
| 816 322 | 1/1988 | European Pat. Off. . |
| 815 833 | 1/1998 | European Pat. Off. . |
| 7-179328 | 7/1995 | Japan . |
| WO 93/07853 | 4/1993 | WIPO . |
| 97/30687 | 8/1997 | WIPO . |
| WO97/30687 | 8/1997 | WIPO . |

OTHER PUBLICATIONS

John D. Pierce, Jr. et al., Cross–adaptation of sweaty–smelling 3–methyl–2–hexenoic acid by its ethyl esters is determined by structural similarity, J. Soc. Cosmet. Chem., 47:363–375 (Nov./Dec. 1996).

*Primary Examiner*—Shelly A. Dodson
*Assistant Examiner*—Marina Lamm
*Attorney, Agent, or Firm*—Fish & Richardson P.C.

[57] ABSTRACT

Disclosed are α-amides of L-amino acids that produce fragrance or attenuate or mask malodor. In particular, glutamine and asparagine amides can be used in the invention. Such α-amides of L-amino acids are useful for generating pleasant fragrances or attenuating or masking malodor upon cleavage of the α-amides of L-amino acids by bacteria in axillae. The α-amides of L-amino acids can be incorporated into skin treatment compositions and personal care products, such as deodorants, body sprays and antiperspirants, and used in methods for producing fragrance or attenuating or masking malodor.

21 Claims, No Drawings

α-AMIDES OF L-AMINO ACIDS AS FRAGRANCE PRECURSORS

BACKGROUND OF THE INVENTION

The invention relates to α-amides of L-amino acids that are precursors of fragrances and which are useful in the formulation of deodorants, antiperspirants, body sprays, and other skin treatment compositions.

In humans, axillary malodors are produced by enzymatic cleavage of malodor precursors found in apocrine secretions. The enzymes that release the malodors are produced by axillary bacteria such as *Staphylococcus sp.* and *Corynebacteria*. Typical deodorants mask or decrease this malodor.

SUMMARY OF THE INVENTION

It has now been shown that various α-amides of L-amino acids can be cleaved by axillary bacterial enzymes, releasing pleasant fragrances and/or attenuating malodor. Such amino acid amides, therefore, are useful in skin treatment compositions such as deodorants, antiperspirants, and body sprays. Accordingly, the invention relates to α-amides of L-amino acids that are precursors of fragrances, or which can attenuate or mask malodor.

In one aspect, the invention features a skin treatment composition (e.g., a deodorant composition) for application to human skin; the skin treatment composition includes a dermatologically acceptable vehicle and an α-amide of an L-amino acid having the structure:

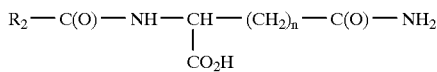

wherein n is 1 or 2 and $R_2$ is selected so that cleavage of the α-amide of the L-amino acid leaves an $R_2$-$CO_2H$ having a neutral or pleasant odor, or which is useful in attenuating or masking malodor. In general, these α-amides of L-amino acids are cleaved by bacterial enzymes by the reaction shown below.

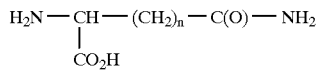

The α-amide of the L-amino acid is present in an amount sufficient to produce fragrance or attenuate or mask malodor. Preferably, the α-amide of L-amino acid is present in the skin treatment composition at a concentration of 0.01 to 10.0% (preferably 0.1 to 5.0%) by weight. If desired, the skin treatment composition can include an antiperspirant active (e.g., aluminum chlorohydrate) or a deodorant active (e.g., an antimicrobial). In various preferred embodiments, the skin treatment composition is formulated as a lotion, cream, stick, gel, or aerosol.

The composition may be formulated as a skin moisturizer, shampoo, shave preparation, body spray, body wash, soap, and the like.

The invention offers several advantages. For example, when the α-amides of L-amino acids are formulated as skin treatment compositions, fragrance is released slowly over time. Consequently, the fragrance is long-lasting and fading of the scent over time is minimized. In many instances, the α-amide of L-amino acids competes with the malodor precursor and attenuates malodor production over a prolonged period.

Other features and advantages of the invention will be apparent from the following detailed description, and from the claims.

DESCRIPTION OF THE PREFERRED EMBODIMENTS

In preferred α-amides of L-amino acids, $R_2$ has 1 to 30 carbon atoms and is alkyl, alkenyl, alkynyl, cycloalkyl, cycloalkenyl, aryl or heterocyclic. These groups may be unsubstituted or substituted with one or more halo, hydroxyl, amino, nitro, amide, alkoxyl, carboxyl, cyano, thio, phosphoro, or other heteroatoms, phenyl, or heterocyclic groups. The amino, amide, alkoxyl, carboxyl, thio, phosphoro, or heterocyclic groups may be unsubstituted or substituted with one or more halo, hydroxyl, amino, nitro, alkyl, amide, alkoxyl, carboxyl, cyano, thio, or phosphoro groups.

$R_2$ can be, for example, methyl, ethyl, propyl, isopropyl, tert-butyl, sec-butyl, isobutyl, n-butyl, pentyl, hexyl, heptyl, octyl, 2-octyl, nonyl, 2-nonyl, decyl, 2-decyl, undecyl, 2-undecyl, dodecyl, tridecyl, tetradecyl, pentadecyl, hexadecyl, heptadecyl, or octadecyl, or a mono or poly unsaturated form thereof, cyclopentyl, cyclohexyl, 2-cyclohexylethyl, 2,6-dimethylheptyl, geranyl, neryl, citronellyl, 9-decenyl, 2,6-dimethyl-5-heptenyl, 2,6-dimethyl-1,5-heptadienyl, 8,11-heptadecadienyl, 8-heptadecenyl, cyclopentenyl, cyclohexenyl, phenyl, p-methoxyphenyl, benzyl, 2-phenylethyl, 1-phenylethyl, 2-(p-methoxyphenyl)-ethenyl, 3-(p-methylphenyl)-2-propyl, 3-(p-isopropylphenyl)-2-propyl, 3-(p-tert-butylphenyl)-2-propyl,2,5,8-trioxanonyl, acetonyl, aminomethyl, hydroxymethyl, 1-hydroxyethyl, dimethylaminomethyl, 1-phenyl-1-aminoethyl, carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl, 10-carboxy-2,5,8-trioxanonyl, 7-carboxamido-5-carboxy-4-aza-3-oxo-heptyl, 8-carboxamido-6-carboxy-5-aza-4-oxo-octyl, 9-carboxamido-7-carboxy-6-aza-5-oxo-nonyl, 10-carboxamido-8-carboxy-7-aza-6-oxo-decyl, 11-carboxamido-9-carboxy-8-aza-7-oxo-undecyl, 14-carboxamido-12-carboxy-11-aza-10-oxo-tetradecyl, 2-pentyl-cyclopropyl, menthyl, or terpineyl.

Preferred α-amides of L-amino acids for use in the invention include, without limitation, N-methylpentenylglutamine, N-methylpentenylasparagine, N-phenylacetylglutamine, N-phenylacetylasparagine, N-indolacetylglutamine, N-indolacetylasparagine, N-cyclohexylcarboxylglutamine, N-cyclohexylcarboxylasparagine, N-ethylbutyrylglutamine, N-ethylbutyrylasparagine, N-phenylpropionylglutamine, N-phenylpropionylasparagine, N-benzoylglutamine, N-benzoylasparagine, N-cyclohexylacetylglutamine, N-cyclohexylacetylasparagine, N-vanilloylglutamine, and N-vanilloylasparagine.

The preferred α-amides of L-amino acids generally can be prepared by coupling a carboxylic acid to a protected amino acid by known procedures. The carboxylic acids and protected amino acids generally are known in the art; they generally are either commercially available or can be made by known procedures.

Examples

Various α-amides of L-amino acids were synthesized and tested for cleavage by *Staphylococcus haemolyticus,* which is commonly found on human skin, especially in the axilla.

In the following examples, amide analogs of the amino acid glutamine in which $R_2$ was phenylacetic acid (PAA) or methylpentenoic acid (MPA) were synthesized. Other known fragrant carboxylic acids (e.g., ethylbutyric acid, cyclohexylcarboxylic acid, or indole-3-acetic acid) can be substituted for PAA or MPA. The α-amides of the L-amino acids were synthesized as described below. The following working examples also provide general guidance for synthesis and testing of other α-amides of L-amino acids in accordance with the invention. These examples are meant to illustrate, not limit, the invention, the metes and bounds of which are defined by the claims.

Synthesis of α-Amides of L-Amino Acids

Coupling Carboxylic Acids to Protected Amino Acids

To couple the carboxylic acid to a protected amino acid. (e.g. L-glutamine t-butylester. HCl) the carboxylic acid (7.4 mmol), the protected amino acid (7.1 mmol), 4-dimethylaminopyridine (0.1 g), diisopropylethylamine (0.92 g, 7.1 mmol) and methylene chloride (40 mL) were stirred, under nitrogen in a 100 mL flask, until the amino acid was dissolved. The reaction was cooled in an ice-water bath and a solution of dicyclohexylcarbodiimide (DCC) (1.5 g, 7.3 mmol) dissolved in methylene chloride (20 mL) was added. Stirring was continued in the ice water bath for approximately 15 minutes, during which time a white precipitate of dicyclohexylurea (DCU) began to form. The reaction was then stirred overnight at room temperature under nitrogen. The following day, the DCU was suction-filtered off, and the filtrate was washed twice with 50 mL of 10% sodium bicarbonate, washed twice with 1M hydrochloric acid (50 ml) then washed once with 50 mL of saturated sodium chloride. The organic layer was dried over anhydrous magnesium sulfate for at least two hours, filtered, and rotary evaporated to dryness. The product can be analyzed with thin layer chromatography (TLC, using silica gel plates) in order to determine the optimal solvent for purification via flash chromatography (e.g., with the FLASH 40 system from Biotage). In general 30–40% ethyl acetate/hexane is suitable. Dissolution of the product prior to chromatography in the eluting solvent may leave additional DCU undissolved, which can be suction-filtered off.

Removal of the t-Butyl Ester Protecting Groups

The protected amino acid (approximately 10 mmol) was dissolved in trifluoroacetic acid (TFA; 25 mL), and the solution was stirred at room temperature for approximately 3 hours (until the reaction was completed, as determined by TLC using the solvents identified for chromatographic purification). The TFA was removed via rotary evaporation and vacuum-oven drying.

In an alternative method, the protected amino acid (10 mmol) was dissolved in ethyl acetate (25 mL), the solution was cooled in an ice-water bath, and hydrogen chloride gas was bubbled into the solution for approximately 15 minutes. The ice-water bath was removed, and the solution was stirred overnight. The solvent then was removed by rotary evaporation and vacuum-oven drying. The products from the reactions were analyzed by TLC on silica gel plates and by $^1$H NMR with a Bruker AC-250 NMR Spectrometer.

Assay of the α-Amides Of L-Amino Acids for Cleavage by Bacteria

The synthesized α-amides of L-amino acids were tested for their ability to be cleaved by bacteria normally found in human axilla. For this example, a 100 mL culture of *Staphylococcus haemolyticus* was grown overnight at 37° C. in Trypticase Soy Broth medium. The cells were pelleted by centrifuging the culture at 5,000 rpm for 12 minutes, and the pelleted cells were resuspended in sterile saline. The cells were again pelleted and resuspended in sterile saline. After pelleting the cells once again, the cells were weighed and resuspended in sterile assay buffer (50 mM phosphate, pH 6.8, 1% glucose/dextran). The final concentration of cells was 0.05 g cells/mL (for the gas chromatography (GC) assay) or 0.1 g cells/mL (for the NMR assay). These cell suspensions can be stored at 4° C.

The α-amides of L-amino acids were prepared as stock solutions at a concentration of approximately 5 mg/mL in 50 mM potassium phosphate buffer (pH 6.8). If necessary, the pH can be adjusted to 6.8–7.0 with 1N NaOH. The amino acid stock solutions were sterilized by filtering them through 0.22 µm filters.

Gas Chromatography Assay

To demonstrate that the α-amides of L-amino acids can be cleaved by bacteria normally found in axilla, a 100 µL aliquot of the α-amides of L-amino acids stock was added to 100 µL of cells in sterile tubes. For a negative control, the cells were incubated with 100 µL sterile phosphate buffer. The samples were incubated for 16–18 hours at 37° C., and the reactions were quenched with 10 µL of 10 N HCl. The samples then were extracted with 100 µL chloroform and analyzed by gas chromatography.

NMR Assay

In addition to analyzing the cleavage reactions by gas chromatography, NMR analysis was used. A 500 µL aliquot of the α-amide of the L-amino acid stock solution was added to 500 µL of cells in sterile tubes. The cells and α-amides of L-amino acids were incubated for 16–18 hours at 37° C., with shaking, and the cleavage reactions were quenched with 50 µL of 10 N HCl. Each sample then was extracted with 600 µL of $CDC_3$, and the extracts were filtered through a $Na_2SO_4$ pipette filter to remove water from the samples. $^1$H NMR spectra of the samples then were taken (64–128 scans generally is sufficient), zooming in on a region that would contain peaks from the cleavage product. The presence or absence of these peaks allowed for a qualitative determination of whether the α-amides of L-amino acids was cleaved. Each of the α-amides of L-amino acids (Phenylacetylglutamine and Methylpentenylglutamine) was cleaved by the *Staphylococcus haemolyticus* cells, as determined by gas chromatography or $^1$H NMR. Thus, these α-amides of L-amino acids can be used as fragrance precursors in skin treatment compositions, for example.

Formulation of Skin Treatment Compositions

A variety of skin treatment (e.g., deodorant or antiperspirant) compositions are known in the art, and the α-amides of L-amino acids of the invention can be used in the formulation of such skin treatment compositions. A variety of skin treatment compositions can be made that include an effective amount of the α-amides of L-amino acids in a dermatologically acceptable vehicle. Such vehicles for use in deodorant or antiperspirant compositions and other ingredients that can be used in deodorant or antiperspirant compositions are known in the art. A preferred form is one containing a deodorant active (e.g. an antimicrobial). Another preferred form is one containing an antiperspirant active. The α-amides of L-amino acids of the invention are used in an amount sufficient to produce fragrance or attenuate or mask malodor when the skin treatment composition is applied topically to skin. Suitable formulations also are well known in the art. Generally, the α-amides of L-amino acids are used at a concentration of 0.01 to 10% by weight. A single α-amide of an L-amino acid can be used in a skin treatment composition, or multiple α-amides of L-amino acids can be used in combination.

Examples of suitable deodorant actives include, without limitation, triclosan, triclocarban, zinc phenolsulfonate, other zinc salts, lichen extract, and usnic acid. Examples of suitable antiperspirant actives include, without limitation, salts of aluminum chlorohydrate; aluminum sesquichlorohydrate, aluminum dichlorohydrate, aluminum chlorohydrex PG or PEG, aluminum sesquichlorohydrex PG or PEG, aluminum dichlorohydrex PG or PEG, aluminum zirconium trichlorohydrate, aluminum zirconium tetrachlorohydrate, aluminum zirconium tetrachlorohydrex PG or PEG, aluminum zirconium pentachlorohydrate, aluminum zirconium octachlorohydrate, aluminum zirconium trichlorohydrex-gly, aluminum zirconium tetrachlorohydrex-gly, aluminum zirconium pentachlorohydrex-gly, aluminum zirconium octachlorohydrex-gly, aluminum zirconium chloride, aluminum zirconium sulfate, potassium aluminum sulfate, sodium aluminum chlorohydroxylacetate, and aluminum bromohydrate. These deodorant or antiperspirant actives can be incorporated into the compositions in accordance with conventional methods for producing deodorants.

Methods for preparing various suitable skin treatment compositions are known in the art. Various deodorant, antiperspirant, and personal care compositions are within the invention; several examples are provided below.

| Ingredients | % w/w |
|---|---|
| Deodorant Stick | |
| Propylene glycol | 70.300 |
| Water | 20.500 |
| Sodium Stearate | 7.000 |
| Triclosan | 0.300 |
| Fragrance | 1.400 |
| α-amide of L-amino acid | 0.50 |
| Total | 100.00 |
| Aerosol Antiperspirant | |
| Cyclomethicone | 10.0 |
| Dimethicone | 2.0 |
| Cyclomethicone (and) Quaternium 18 Hectorite (and) SDA 40 | 2.0 |
| SDA 40, Anydrous | 0.5 |
| Aluminum Chlorohydrate | 10.0 |
| α-amide of L-amino acid | 1.0 |
| Propellant A-31 | 74.5 |
| Total | 100.00 |
| Suspension Antiperspirant Stick | |
| Cyclomethicone | 54.5 |
| Stearyl Alcohol | 20.0 |
| PPG-14 Butyl Ether | 2.0 |
| Hydrogenated Castor Oil | 1.0 |
| Talc | 2.0 |
| Aluminum Zirconium Tetrachlorohydrex-Gly | 20.0 |
| α-amide of L-amino acid | 0.5 |
| Total | 100.00 |

| Ingredients | % w/w |
|---|---|
| -continued | |
| Anydrous Roll-On Antiperspirant | |
| Cyclomethicone | 69.0 |
| Dimethicone | 5.0 |
| Cyclomethicone (and) Quaternium 18 Hectorite (and) SDA 40 | 3.0 |
| SDA 40, Anydrous | 2.0 |
| Aluminum Zirconium Tetrachlorohydrex-Gly | 20.0 |
| α-amide of L-amino acid | 1.0 |
| Fragrance Oil | q.s. |
| Total | 100.00 |
| Transparent Antiperspirant Gel | |
| Phase A | |
| Cyclomethicone (and) Dimethicone Copolyol | 10.0 |
| Cyclomethicone | 7.0 |
| Phase B | |
| Aluminum Chlorohydrate (and) Water | 50.0 |
| Propylene Glycol | 16.0 |
| Water | 16.0 |
| α-amide of L-amino acid | 1.0 |
| Total | 100.00 |
| Nonionic O/W, Emollient Cream | |
| Water | 73.000 |
| Stearic acid | 7.200 |
| Glyceryl monostearate | 4.500 |
| Lanolin | 1.000 |
| Isopropyl myristate | 4.300 |
| Polyethylene glycol 1000 monostearate | 6.000 |
| α-amide of L-amino acid | 1.00 |
| Preservative | 0.300 |
| Perfume | 0.200 |
| Total | 100.00 |

Other Embodiments

If desired, the α-amides of L-amino acids can be used in combination with other fragrance producing molecules or perfumes as indicators that the products are working, or to enhance the fragrance. In addition, the α-amides of L-amino acids can be used in personal care compositions to produce fragrance or attenuate or mask malodors.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for application to human skin comprising a dermatologically acceptable vehicle and an α-amide of an L-amino acid having the structure:

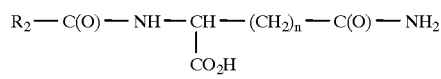

wherein:
the α-amide of the L-amino acid is present in an amount sufficient to produce fragrance or attenuate or mask malodor;

n is 1 or 2; and

R₂ is selected so that cleavage of the α-amide of an L-amino acid leaves an R₂–CO₂H having a neutral or pleasant odor.

2. The composition of claim 1, wherein R₂ has 1 to 30 carbon atoms and is selected from the group consisting of alkyl, alkenyl, alkynyl, cycloalkyl, cycloalkenyl, aryl, or heterocyclic, wherein each of these may be unsubstituted or substituted with one or more halo, hydroxyl, amino, nitro, amide, alkoxyl, carboxyl, cyano, thio, phosphoro, phenyl, or heterocyclic groups, wherein the amide, amino, alkoxyl, carboxyl, thio, phosphoro, phenyl, or heterocyclic groups may be unsubstituted or substituted with one or more halo, hydroxyl, amino, nitro, amide, alkoxyl, carboxyl, cyano, thio, phosphoro, phenyl, and heterocyclic groups.

3. The composition of claim 2, wherein R₂ is selected from the group consisting of methyl, ethyl, propyl, isopropyl, tert-butyl, sec-butyl, isobutyl, n-butyl, pentyl, hexyl, heptyl, octyl, 2-octyl, nonyl, 2-nonyl, decyl, 2-decyl, undecyl, 2-undecyl, dodecyl, tridecyl, tetradecyl, pentadecyl, hexadecyl, heptadecyl, octadecyl, or a mono or poly unsaturated form thereof, cyclopentyl, cyclohexyl, 2-cyclohexylethyl, 2,6-dimethylheptyl, geranyl, neryl, citronellyl, 9-decenyl, 2,6-dimethyl-5-heptenyl, 2,6-dimethyl-1,5-heptadienyl, 8,11-heptadecadienyl, 8-heptadecenyl, cyclopentenyl, cyclohexenyl, phenyl, p-methoxyphenyl, benzyl, 2-phenylethyl, 1-phenylethyl, 2-(p-methoxyphenyl)-ethenyl, 3-(p-methylphenyl)-2-propyl, 3-(p-isopropylphenyl)-2-propyl, 3-(p-tert-butylphenyl)-2-propyl,2,5,8-trioxanonyl, acetonyl, aminomethyl, hydroxymethyl, 1-hydroxyethyl, dimethylaminomethyl, 1-phenyl-1-aminoethyl, carboxymethyl, 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl, 10-carboxy-2,5,8-trioxanonyl, 7-carboxamido-5-carboxy-4-aza-3-oxo-heptyl, 8-carboxamido-6-carboxy-5-aza-4-oxo-octyl, 9-carboxamido-7-carboxy-6-aza-5-oxo-nonyl, 10-carboxamido-8-carboxy-7-aza-6-oxo-decyl, 11-carboxamido-9-carboxy-8-aza-7-oxo-undecyl, 14-carboxamido-12-carboxy-11-aza-10-oxo-tetradecyl, 2-pentyl-cyclopropyl, menthyl, or terpineyl.

4. The composition of claim 1, wherein the α-amide of the L-amino acid is selected from the group consisting of N-methylpentenylglutamine, N-methylpentenylasparagine, N-phenylacetylglutamine, N-phenylacetylasparagine, N-indolacetylglutamine, N-indolacetylasparagine, N-cyclohexylcarboxylglutamine, N-cyclohexylcarboxylasparagine, N-ethylbutyrylglutamine, N-ethylbutyrylasparagine, N-phenylpropionylglutamine, N-phenylpropionylasparagine, N-benzoylglutamine, N-benzoylasparagine, N-cyclohexylacetylglutamine, N-cyclohexylacetylasparagine, N-vanilloylglutamine, and N-vanilloylasparagine.

5. The composition of claim 4, wherein the α-amide of the L-amino acid is N-methylpentenylglutamine.

6. The composition of claim 4, wherein the α-amide of L-amino acid is N-methylpentenylglutamine.

7. The composition of claim 1, wherein n is 1.

8. The composition of claim 1, wherein n is 2.

9. The composition of claim 1, wherein the α-amide of the L-amino acid is present at a concentration of 0.01–10.0% by weight.

10. The composition of claim 1, 7, or 8, further comprising an antiperspirant active.

11. The composition of claim 1, 7, or 8, further comprising a deodorant active.

12. The composition of claim 1 in the form of a lotion, cream, stick, gel, or aerosol.

13. The composition of claim 10 in the form of a lotion, cream, stick, gel, or aerosol.

14. The composition of claim 11 in the form of a lotion, cream, stick, gel, or aerosol.

15. A method for producing fragrance or attenuating or masking malodor, the method comprising applying the composition of claim 1, 7, or 8 to skin of a human.

16. A method for producing fragrance or attenuating or masking malodor, the method comprising applying the composition of claim 1, 7, or 8 to the axilla of a human.

17. A method for producing fragrance or attenuating or masking malodor, the method comprising applying the composition of claim 10 to skin of a human.

18. A method for producing fragrance or attenuating or masking malodor, the method comprising applying the composition of claim 11 to skin of a human.

19. The composition of claim 1, wherein the composition is selected from the group consisting of skin moisturizers, shampoos, body washes, soaps, shave preparations, and body sprays.

20. The composition of claim 19, wherein the α-amide of L-amino acid is present at a concentration of 0.01–10.0% by weight.

21. A method for producing fragrance or attenuating or masking malodor, the method comprising applying the composition of claim 19 to skin of a human.

* * * * *

UNITED STATES PATENT AND TRADEMARK OFFICE
CERTIFICATE OF CORRECTION

PATENT NO.     : 5,932,198
DATED          : August 3, 1999
INVENTOR(S)    : Virginia Goldman et al.

It is certified that error appears in the above-identified patent and that said Letters Patent is hereby corrected as shown below:

Title page, column 1,
Line 21, delete "Nicholas" and insert -- Nichols --

Title page, column 2,
Line 1, delete "1998" and insert -- 1998 --

Signed and Sealed this

Twenty-fifth Day of September, 2001

*Attest:*

*Attesting Officer*

NICHOLAS P. GODICI
*Acting Director of the United States Patent and Trademark Office*